United States Patent
Penu et al.

(10) Patent No.: US 9,850,224 B2
(45) Date of Patent: Dec. 26, 2017

(54) PRODUCTION OF MESO-LACTIDE, D-LACTIDE, AND L-LACTIDE BY BACK BITING OF POLYLACTIDE

(71) Applicant: FUTERRO S.A., Escanaffles (BE)

(72) Inventors: Christian Penu, Saint Saulve (FR); Benjamine Belloncle, Onnaing (FR)

(73) Assignee: Futerro S.A., Escanaffles (BE)

( * ) Notice: Subject to any disclaimer, the term of this patent is extended or adjusted under 35 U.S.C. 154(b) by 0 days.

(21) Appl. No.: 15/102,825

(22) PCT Filed: Dec. 9, 2014

(86) PCT No.: PCT/EP2014/077077
§ 371 (c)(1),
(2) Date: Jun. 8, 2016

(87) PCT Pub. No.: WO2015/086614
PCT Pub. Date: Jun. 18, 2015

(65) Prior Publication Data
US 2016/0311793 A1 Oct. 27, 2016

(30) Foreign Application Priority Data
Dec. 10, 2013 (EP) .................................. 13196418

(51) Int. Cl.
| | | |
|---|---|---|
| *C08G 63/08* | (2006.01) |
| *C07D 319/12* | (2006.01) |
| *C08G 18/42* | (2006.01) |
| *B01J 23/02* | (2006.01) |
| *B01J 27/24* | (2006.01) |
| *B01J 31/02* | (2006.01) |
| *B01J 31/04* | (2006.01) |
| *B01J 31/26* | (2006.01) |
| *C04B 16/06* | (2006.01) |
| *C09D 167/04* | (2006.01) |

(52) U.S. Cl.
CPC ............ *C07D 319/12* (2013.01); *B01J 23/02* (2013.01); *B01J 27/24* (2013.01); *B01J 31/0267* (2013.01); *B01J 31/0274* (2013.01); *B01J 31/04* (2013.01); *B01J 31/26* (2013.01); *C08G 18/428* (2013.01); *B01J 2231/52* (2013.01); *B01J 2531/002* (2013.01); *B01J 2531/004* (2013.01); *B01J 2531/007* (2013.01); *C04B 16/0683* (2013.01); *C09D 167/04* (2013.01)

(58) Field of Classification Search
CPC ............ C04B 16/0683; B01J 31/0274; C08G 18/428; C09D 167/04
See application file for complete search history.

(56) References Cited

U.S. PATENT DOCUMENTS

| | | |
|---|---|---|
| 2013/0023674 A1 | 1/2013 | Narayan et al. |
| 2013/0096342 A1* | 4/2013 | Srinivasan .............. C07C 51/09 562/589 |

FOREIGN PATENT DOCUMENTS

| | | | |
|---|---|---|---|
| BE | WO 2010/079233 | * | 7/2010 |
| EP | 2559725 A1 | | 8/2011 |
| EP | 2607399 A1 | | 6/2013 |
| FR | 2691380 | | 5/1992 |
| JP | 2008/201679 | | 9/2008 |
| WO | WO 2014/000277 A1 | | 1/2014 |

OTHER PUBLICATIONS

Ibragimov (Catalysis, http://www.thermopedia.com/content/618/), Article added Feb. 2, 2011.*
Noda M et al.; "Thermal catalytic depolymerization of . . . "; Chemical and Pharmaceutical; Bulletin, Pharmaceutical Society of Japan, JP, vol. 47, No. 4, Apr. 1, 1999 (Apr. 1, 1999), pp. 467-471, XP002989188, ISSN: 0009-2363.

* cited by examiner

*Primary Examiner* — Gregory Listvoyb
(74) *Attorney, Agent, or Firm* — Reinhart Boerner Van Deuren P.C.

(57) ABSTRACT

Process for increasingly producing D-Lactide and meso lactide by depolymerizing by back biting polylactide (PLA) said process which comprises: (i) Depolymerizing polylactide into its corresponding dimeric cyclic esters by heating the polylactide in the presence of a catalyst system comprising a catalyst and a co-catalyst in a reaction zone at temperature and pressure at which the polylactide is molten; (ii) Forming a vapor product stream from the reaction zone; (iii) Removing the vapor product stream and optionally condense it; (iv) Recovering, either together or separately meso-lactide, D-lactide and L-lactide.

5 Claims, 1 Drawing Sheet

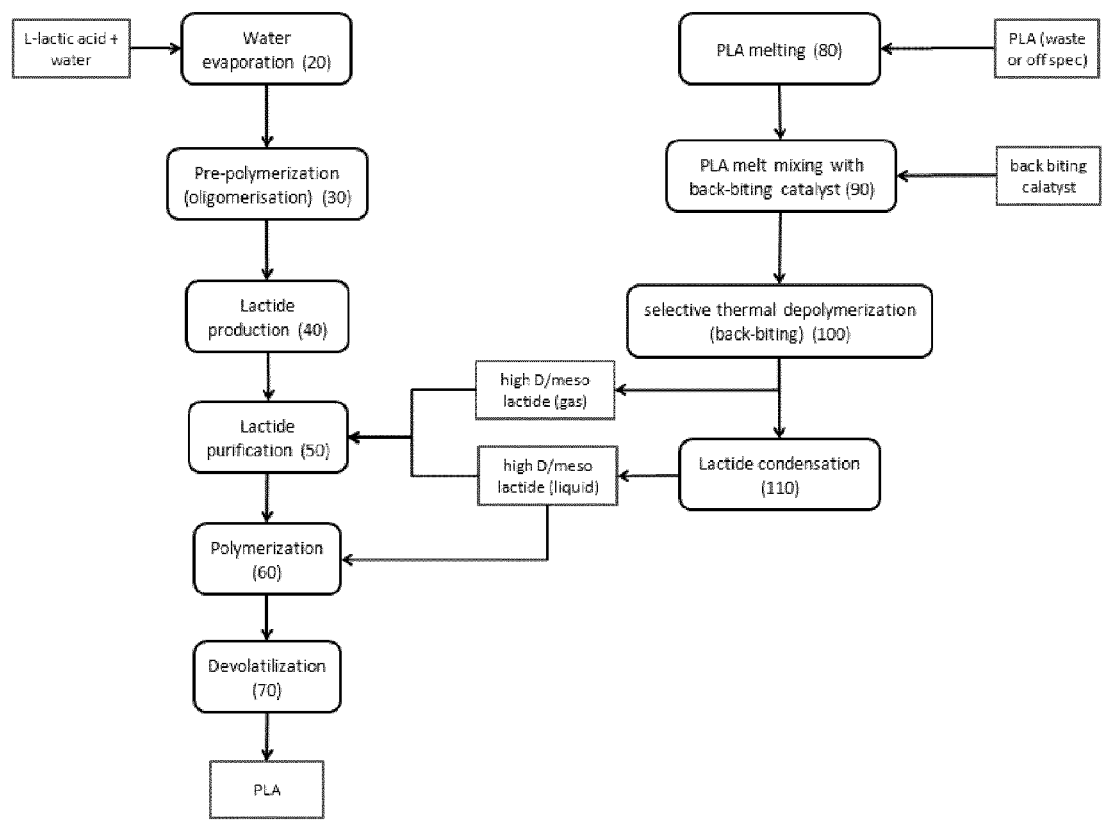

PRODUCTION OF MESO-LACTIDE, D-LACTIDE, AND L-LACTIDE BY BACK BITING OF POLYLACTIDE

The present invention relates to a recycling depolymerization process (also called back biting process) wherein high molecular weight aliphatic polyester or co-polyester and particularly solid polylactide, oligomers of polylactide are recycled for depolymerization and to the recovery of the hydrocarboxylic values thereby in the form of cyclic esters.

More particularly the process of the invention is an improved depolymerization process to selectively produce meso-lactide, and D-lactide in addition to the expected L-lactide.

Within the frame of the production of polylactide (PLA) which is a biodegradable polymer, it becomes more and more important to be able to prepare copolymers with different contents of D-lactide.

While it is known that D-lactide may currently be obtained by fermentation of lactic acid of the D-configuration, it is also possible to recover D-lactide or meso-lactide starting from PLA after a depolymerization treatment of it.

It is therefore of importance to develop a new way, rather than, starting with lactic acid, to increasingly produce D-lactide and meso-lactide in order to prepare PDLA or copolymers containing both L and D-lactic acid enantiomer to form copolymers having different proportions of D and L units.

There is thus a need for such a process.

Normally and conveniently, the polymer or mixture of polymers subject to the depolymerization process comprises higher polymeric polylactide and is heated to produce cyclic esters. Such a process is generally very slow. On top of that those depolymerization processes are focused more on the purity of the lactide to recover than on a racemization to produce the other enantiomer.

WO2014/000277 discloses a method for using a recycled polylactic acid to prepare lactide. The method comprises a) crushing recycled polylactic acid, b) melting and extruding the crushed recycled polylactic acid and entering the melt into a pre-depolymerization reactor to obtain a polylactic acid melt, c) making said melt undergo a chain scission reaction at 180° C. to 250° C. with a catalyst to break the molecular chain of the melt (Mn<5000), d) making the polylactic acid melt with broken chains undergo a depolymerization reaction at 150° C. to 250° C. with the degree of vacuum being −0.1 MPa to −0.09 MPa, to produce crude lactide, e) separating the crude lactide through melt crystallization to obtain refined lactide. The content of the lactide can reach higher than 99.5% and the optical purity can reach higher than 99.9%.

The Chemical and Pharmaceutical bulletin, Pharmaceutical Society of Japan, vol. 47, n° 4, Apr. 1, 1999, pages 467-471 discloses a series of Al, Ti, Zn and Zr compounds which were evaluated as intramolecular transesterification catalysts for the thermal depolymerization reaction of poly (L-lactic acid) oligomer resulting in LL-lactide, meso-lactide and DD-lactide.

EP 2 607 399 discloses a process for producing polylactic acid and reactors for use in said process. Example 2 refers to a depolymerization process of polylactic acid oligomer with tin oxide catalyst.

US 2013/0023674 provides a method for the production of lactide directly from recycled PLA wastes using thermal depolymerization process. Such depolymerization was exemplified in the presence of Ti (II) catalyst. The product recovered was mainly L-lactide.

Different patents, like Japanese Patent 2008-201679, also relate to the use of a catalytic system comprising in addition to the catalyst an acid compound, without other restriction, in order to improve depolymerization.

A need exists therefore for an improved process for depolymerizing polylactide, particularly and selectively to cyclic esters, i.e., D-lactide, meso-lactide and L-lactide.

SUMMARY OF THE INVENTION

The present invention provides for a process for depolymerizing (by back biting) polylactide (PLA) into its corresponding dimeric cyclic esters and increasingly producing D-lactide and meso-lactide, said process which comprises
(i) Depolymerizing the polylactide (PLA) into its corresponding dimeric cyclic esters by heating the polylactide in the presence of a catalyst system in a reaction zone at temperature and pressure at which the polylactide is molten;
(ii) Forming a vapor product stream from the reaction zone;
(iii) Removing the vapor product stream and optionally condense it;
(iv) Recovering either together or separately meso-lactide, D-lactide and L-lactide.

When used in the present invention, the terms increasingly producing are meaning the production of an increased amount of D-lactide and meso-lactide over that generally recoverable with usual process, and particularly when starting with polylactide prepared from lactic acid having from 80% to 98.5% by weight of L-units and/or even with polylactide prepared from lactic acid having more than 98.5% by weight of L-units. Such amount may reach up to 35% by weight of D-lactide and meso-lactide, or even more (i.e. 55% by weight, when starting with lactic acid having a L-enantiomer content not exceeding 80% by weight).

According to the process of the present invention, to increasingly produce D-lactide and meso-lactide from depolymerization of polylactide is to heat said polylactide in a reaction zone, at a temperature comprised between 200 and 290° C., and preferably between 210 and 260° C., under reduced pressure, in the presence of a catalyst system, so enabling the formation of a vapor product stream containing lactide which is then distilled off.

The polyester, co-polyester to be depolymerized in accordance with the process of the invention is an aliphatic polyester, or co-polyester, particularly polylactide, prepared from lactic acid having from 80% to 98.5% by weight of L units, and/or polylactide, prepared from lactic acid having more than 98.5% by weight of L-units; said polyesters are characterized by a weight average molecular weight (Mw) lying between 500 and 500,000 Dalton, particularly 30,000 and 300,000 Dalton, more preferably 80,000 and 200,000 Dalton and having a ratio of the weight average molecular weight (Mw) to the number average molecular weight (Mn) called molecular weight distribution (MWD) of less than 2.0. The weight average and number average molecular weight were measured by chromatography by gel permeation compared to a standard polystyrene in chloroform at 25° C. Measurement of the molecular masses may be performed at 25° C. using a liquid chromatograph WATERS 610. Firstly, a polymer solution is prepared in chloroform (1 mg polymer/ml). Then, 100 µl of this solution is taken and injected, through a filter with pores of 0.2 µm diameter, on the chromatograph column at 25° C. Molecular masses are determined from the retention time in the column, translated in mass equivalent using a universal calibration law based on polystyrene standards. For example, ASTM practice D3016-97(2010) may be used.

The catalyst system to be used in the process of the present invention generally comprises a catalyst and a co-catalyst; the catalyst is general formula (M)(X1, X2, ... Xm)n where M is a metal selected from the group comprising the elements of columns 3 to 12 of the periodic table of the elements as well as the elements Al, Ga, In, Ti, Ge, Sn, Pb, Sb, Bi, Ca and Mg, preferably from Sn, Zn and Mg and X1, X2 ... Xm are each substituents selected from one of the classes of alkyls, aryls, oxides, carboxylates, halogenides, alkoxides as well as elements of columns 15 and/or 16 of the periodic table, <<m>> is an integer ranging from 1 to 6 and <<n>> is an integer ranging from 0 to 6; the co-catalyst is selected from the group comprising (a) organic or inorganic acids having a dissociation constant, pKa, around that of lactic acid which is for information of 3.86, and particularly comprised between 3.0 and 4.7, preferably between 3.5 and 4.2, more preferably between 3.7 and 3.9; (b) a compound of general formula (Y)(R1, R2, ..., Rq)p, where Y is an element selected from the group comprising the elements of columns 15 or 16 of the periodic table of the elements and particularly Phosphorus, and where R1, R2, ... Rq are each substituents selected from one of the classes of alkyls, aryls, oxides, halogenides, oxyalkyls, aminoalkyls, thioalkyls, phenoxides, aminoaryls, and thioaryls, <<q>> is an integer ranging from 1 to 6 and <<p>> is an integer ranging from 0 to 6; and (c) an organosilane aliphatic or cycloaliphatic selected from the group comprising alkyl alkoxysilane or the cycloalkylalkoxysilane represented by the general formula QQ'Si(O-alkyle)$_2$, where the Q and Q' are the same or different and are alkyl or cycloalkyl radical containing from 1 to 8 carbon atoms.

Among the cocatalysts selected from the group comprising organic or inorganic acids one can cite for example the fumaric acid, the lactic acid and the glycolic acid.

Among the cocatalysts selected from the group comprising a compound of general formula (Y)(R1, R2, ..., Rq)p one can cite for example triphenylphosphine.

Among the cocatalysts selected from the group comprising an organosilane aliphatic or cycloaliphatic one can cite for example dicyclopentyldimethoxysilane, cyclohexylmethyldimethoxysilane, diisobutyldimethoxysilane and t-butylethyldimethoxysilane.

The catalyst of the catalyst system is used in an amount comprised between 0.05 and 3% by weight of the PLA, preferably between 0.1 and 2% by weight and the co-catalyst is generally used in an amount comprised between 0.1 and 10.0% and preferably between 1.0 and 8.0% by weight of the PLA.

In the present invention the main ingredient of the feed to be treated by depolymerisation is PLA and it represents at least 60% by weight, preferably 80% by weight of the feed to depolymerize.

For the present invention PLA means polylactide or polylactic acid and represents poly-L-lactic acid (PLLA), poly-D-lactic acid (PDLA) and polylactic acid of racemic L- and D-; it also comprises polylactic acid stereocomplex as well as PLA-urethane copolymers.

In carrying out the process of the invention, the feed containing the PLA is first subject to a thermal decomposition at temperature comprised between 200 and 290° C., preferably between 210 and 260° C. and either at a reduced pressure generally under lactide vapour pressure, or by carrying away with an inert gas like nitrogen, and in the presence of a catalytic system.

The Applicants have now found that to favorize the production of D-lactide and meso-lactide, the temperature has to be controlled carefully. Indeed, below 200° C., when applying the process of the invention in the presence of the catalyst system, the final yield in D-lactide and meso-lactide is very low and therefore does not present interest. It may be said, that even for the recovery of L-lactide the yield is not significantly high. On the other hand, when using temperatures higher than 290° C., there appears a certain degradation of the products, so lowering drastically the yield in D-lactide and meso-lactide.

It is therefore unexpected that in a certain range of temperatures in the depolymerization step, in combination with the use of the co-catalyst, the Applicants obtained so high production of D-lactide and meso-lactide, even when starting with PLLA for which their content in the starting material is very low.

According to an embodiment of the process of the invention, the mixture of polymers containing PLA is therefore introduced in a reaction zone where it is heated to depolymerize. The vapors formed during said reaction, or back biting, are then condensed and then recovered separately. The duration of the heating step will depend of the reaction temperature.

The catalytic system is introduced together with the mixture of polymers in the reaction zone and comprises any catalyst enabling the thermolysis of PLA into cyclic esters. Suitable catalysts are generally metals or compounds of metals of columns 3 and 12 of the periodic table of the elements and of Mg and Sn; typical catalysts in the catalyst system are preferably selected from the group comprising Sn(II) carboxylates like Sn octanoate, MgO, ZnO, or even a mixture thereof.

According to the process of the present invention, the Applicant have now found interesting results are obtained to produce selectively D-lactide and meso-lactide even when starting with PLLA (more than 98.5% by weight of L-configuration) rather than with normal polylactide (between 80 and 90% by weight of L-configuration), if a suitable combination of the depolymerization temperature is applied together with the presence of a co-catalyst selected from either an organic or inorganic acid having a dissociation constant, pKa, ranging between 3.0 and 4.7, preferably between 3.5 and 4.2 and more preferably between 3.7 and 3.9, or a phosphorus compound, preferably triphenylphosphine, or an alkoxysilane derivatives, the depolymerization temperature ranging between 210° C. and 260° C. Typical depolymerization times may last from a few minutes i.e. 10 min to several hours i.e. 3 h depending on the depolymerization reactor used.

The vapor product stream exiting the reaction zone, normally comprises the dimeric cyclic ester, this means L-lactide, D-lactide and meso-lactide but also other volatiles components. The vapor product is then optionally subjected to a condensation step or further processed as such. The condensed vapor products, if any, are readily separated, by any suitable means in its constituents (e.g. distillation, crystallization ... ).

The Applicants have also found that the association of the catalyst with the co-catalyst has an importance on the racemization of the lactide. Indeed, when using a catalyst system implementing Sn octanoate as catalyst it is preferable to use acids, more preferably organic acids as co-catalyst, having a pKa>4, such as for example fumaric acid (pKa$_2$: 4.44) but among the catalyst system with Sn octanoate as catalyst the preferred co-catalyst is triphenylphosphine (TPP), while with MgO or with a mixture of MgO and ZnO as catalyst the co-catalyst is preferably selected from organic acids having a pKa comprised between 3.0 and 4.0 like lactic acid (pKa: 3.86) or glycolic acid (pKa: 3.88).

When MgO is used as catalyst, one can also use as cocatalyst an organosilane aliphatic or cycloaliphatic selected from the group comprising alkylalkoxysilane or the cycloalkylalkoxysilane represented by the general formula QQ'Si(O-alkyle)$_2$, where the Q and Q' are the same or different and are alkyl or cycloalkyl radical containing from 1 to 8 carbon atoms. Among these cocatalysts, cycloalkylalkoxysilane is preferably used such as for example cyclohexylmethyldimethoxysilane.

Another advantage of the process of the invention is to produce a much more important proportion of D-lactide and meso-lactide during the depolymerization, particularly when the starting material is lactic acid constituted of substantially completely of enantiomer L.

It has been noted that when the process of the invention is integrated in a global process starting with lactic acid to obtain a polymer thereof, it is now feasible to consider that said global process may also integrate the preparation of copolymers containing both enantiomers L and D, by simply introducing D-lactide and meso-lactide together with the L-lactide into the ring opening polymerization reactor.

The process of the invention enables to manufacture any type of in situ copolymers of P(L-D)LA and particularly those whose enantiomer D content being such it may reach 30-35% by weight, while it was not easily feasible in such a way in the prior art processes, except by blends.

FIG. 1 is representing a process to prepare PLA starting with lactic acid containing more than 98.5% by weight enantiomer L, said process starting with an aqueous solution of lactic acid from which water is evaporated to obtain lactic acid which is then prepolymerized and subject to cyclization to form crude L-lactide which needs to be purified before being polymerized by ring opening of lactide, and finally the resulting PLA is purified by devolatilization.

According to the process of the present invention, it is now possible to introduce, at the level of the purification of the crude lactide, a stream either liquid or gaseous, of a mixture rich in meso-lactide and D-lactide resulting from the depolymerization by back biting; said stream rich in meso-lactide and D-lactide is mixed with the stream of L-lactide and both streams are subject together to the ring opening polymerization, in accordance with usual conditions generally applied for such reaction.

So, a copolymer is now formed containing both enantiomers L and D-. These latter being in a proportion which may reach 30 to 35% by weight.

It is understood that lower contents may also be reached, simply by controlling the feeding of the back biting stream in the main stream of crude L-lactide to be purified.

Another advantage of the process of the invention, based on the important proportion of D-lactide and meso-lactide produced during the depolymerization, even if the starting material is constituted substantially completely of enantiomer-L, is to envision an integrated process for the production of homopolymers or copolymers of PLA, i.e., PLLA or PLLA-PDLA, starting with an aqueous solution of lactic acid not containing more than 10% of D-lactic acid.

Such an integrated process is generally consisting of the removal of water from the starting lactic acid aqueous solution, the oligomerization of lactic acid into oligomers of 400 to 5,000 Dalton, the cyclisation of said oligomers to produce crude lactide then subject the obtained crude lactide to purification, and finally the polymerization by ROP of the lactide into PLA.

Owing to the process of the invention which can produce more D-lactide and meso-lactide by depolymerization of PLA waste and off spec of the integrated process, this stream may be introduced directly in the purification step of the lactide of the integrated process, according to which the amount of D-lactide and for meso lactide introduced is controlled in order to achieve the desired composition of copolymers. Generally, the composition of the copolymer may contain up to 25 to 35% by weight of D-lactide and for meso-lactide.

It is agreed that the process of the invention is not limited to such an integrated process, particularly when the feed of the back biting step is comprising waste of PLA coming from other sources than the present process; PLA waste from such sources may of course contain different amount of D-enantiomer which may reach 20% by weight;

EXAMPLES

The back biting of various PLA samples, all having an enantiomer L content of 99.4% by weight has been carried out.

First the samples were ground and then deposited into a recipient (the reaction zone) which was introduced into the reactor. Then the catalyst and co-catalysts were added in the reaction zone. The Sn octanoate (Sn (oct)$_2$) used as catalyst was added in an amount of 1% by weight of the PLA. Regarding the co-catalyst, when fumaric acid was used (pKa$_1$=3.03; pKa$_2$=4.44), it was added in an amount of 5% by weight of the PLA. When triphenylphosphine was used as co-catalyst, it was added in an amount of 0.7% by weight of the PLA.

The temperature was then raised up to 250° C. and maintained during 60 minutes.

The pressure was adjusted to 10 millibar.

During the period of time the reaction mixture was maintained at said temperature, a vapor product was formed and further extracted from the reaction zone while the vapor product was then subject to a condensation step.

The condensed product was recovered and analysed by gas chromatography (GC) to determine its constituents and their respective contents in % by weight in L-lactide, D-lactide and meso-lactide. The lactide yield (%) represents the quantity of lactide recovered and condensed.

The results are presented here below.

| Ex. | Catalyst | Co-Cata | lactide yield (%) | L-lactide (%) | D-lactide (%) | Meso-Lactide (%) | Impurities (%) |
|---|---|---|---|---|---|---|---|
| 1 | Sn (oct)$_2$ | None | 90.7 | 83.3 | 1.7 | 14.0 | 1.0 |
| 2 | Sn (oct)$_2$ | Fumaric Acid | 65.0 | 68.0 | 6.0 | 25.0 | 1.0 |
| 3 | Sn (oct)$_2$ | TPP | 83.8 | 68 | 8.5 | 22.3 | 0.2 |

A comparative example was conducted under the same conditions as those described for the examples according to the invention excepted that the sulfamic acid having a pKa of 0.99 was used as co-catalyst at 5.3% by weight of the PLA.

| Ex. | Catalyst | Co-Cata | lactide Yield (%) | L-lactide (%) | D-lactide (%) | Meso lactide (%) | Impurities (%) |
|---|---|---|---|---|---|---|---|
| 4 | Sn (oct)$_2$ | Sulfamic Acid | 1.1 | 95 | None | 0.9 | 4.1 |

Other examples within the process of the invention were conducted under the same operating conditions as those described above excepted that another catalyst than Sn octanoate and cocatalyst were used. MgO was used as catalyst in an amount of 1% by weight of the PLA and lactic acid (pKa: 3.86) was used as cocatalyst, it was added in an amount of 5% by weight of the PLA (see example 5). In example 6, MgO was used as catalyst in an amount of 1% by weight of the PLA and cyclohexylmethyldimethoxysilane was used as cocatalyst in an amount of 5% by weight of the PLA. In example 7, the same example was conducted without any cocatalyst (comparative example).

| Ex. | Catalyst | Co-Cata | lactide Yield (%) | L-lactide (%) | D-lactide (%) | Meso lactide (%) | Impurities (%) |
|---|---|---|---|---|---|---|---|
| 5 | MgO | Lactic Acid | 81.0 | 70.3 | 11.0 | 18.2 | 0.5 |
| 6 | MgO | cyclohexylmethyl dimethoxysilane | 90.0 | 37.4 | 30.7 | 28.5 | 4.4 |
| 7 | MgO | None | 60.9 | 92.3 | 1.4 | 6.1 | 0.2 |

The invention claimed is:

1. Process for increasingly producing D-Lactide and meso lactide by depolymerizing by back biting polylactide (PLA) said process which comprises:
   (i) Depolymerizing polylactide into its corresponding dimeric cyclic esters by heating the polylactide in the presence of a catalyst system which comprises MgO as catalyst and a cycloalkylalkoxysilane represented by the general formula QQ'Si(O-alkyle)$_2$, where the Q and Q' are different and are alkyl or cycloalkyl radical containing from 1 to 8 carbon atoms as cocatalyst, or wherein the catalyst system comprises MgO as catalyst and cyclohexylmethyldimethoxysilane as cocatalyst in a reaction zone at temperature and pressure at which the polylactide is molten;
   (ii) Forming a vapor product stream from the reaction zone;
   (iii) Removing the vapor product stream and optionally condense it;
   (iv) Recovering, either together or separately meso-lactide, D-lactide and L-lactide.

2. Process according to claim 1, wherein the catalyst of the catalyst system is used in an amount comprised between 0.05 and 3% by weight of PLA and the co-catalyst is used in an amount comprised between 0.1 and 10% by weight of PLA.

3. Process according to claim 1, wherein the depolymerization is carried out at a temperature between 200 and 290° C. and at a pressure under lactide vapour pressure.

4. Process of mixing D-lactide and meso lactide obtained according to claim 1, with L-lactide to prepare a copolymer of P(L-D)LA by ring opening polymerization, the content of enantiomer D- of said copolymer not exceeding 35% by weight.

5. Process according to claim 3, wherein the depolymerization is carried out at a temperature between 210 and 260° C. and at a pressure under lactide vapour pressure.

* * * * *